(12) United States Patent
Funamoto

(10) Patent No.: US 8,780,346 B2
(45) Date of Patent: Jul. 15, 2014

(54) SPECTROSCOPIC IMAGE CAPTURING APPARATUS

(71) Applicant: Seiko Epson Corporation, Tokyo (JP)

(72) Inventor: Tatsuaki Funamoto, Shiojiri (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 13/919,362

(22) Filed: Jun. 17, 2013

(65) Prior Publication Data

US 2014/0002710 A1 Jan. 2, 2014

(30) Foreign Application Priority Data

Jul. 2, 2012 (JP) .................. 2012-148202

(51) Int. Cl.
*G01J 3/447* (2006.01)
(52) U.S. Cl.
USPC ........................................... 356/327
(58) Field of Classification Search
USPC ........................................ 356/300, 326–328
See application file for complete search history.

(56) References Cited

U.S. PATENT DOCUMENTS

| | | | |
|---|---|---|---|
| 5,541,057 A | 7/1996 | Bogart et al. | |
| 5,629,214 A | 5/1997 | Crosby | |
| 5,869,272 A | 2/1999 | Bogart et al. | |
| 6,614,533 B1 | 9/2003 | Hata | |
| 8,063,976 B2 | 11/2011 | Kita | |
| 8,182,425 B2 | 5/2012 | Stamatas et al. | |
| 2010/0211333 A1 | 8/2010 | Pruet et al. | |
| 2011/0181869 A1* | 7/2011 | Yamaguchi et al. | ............ 356/72 |

FOREIGN PATENT DOCUMENTS

| | | |
|---|---|---|
| JP | 05-172748 B2 | 9/1993 |
| JP | 2011-242395 A | 12/2001 |
| JP | 2000-329617 A | 11/2002 |
| JP | 2005-049356 A | 2/2005 |
| JP | 2006-226995 A | 8/2006 |
| JP | 2009-033222 A | 2/2009 |
| WO | WO-93-07801 A1 | 4/1993 |

OTHER PUBLICATIONS

Extended European Search Report for Application No. EP 13 17 4298 mailed September 18, 2013 (6 pages).

* cited by examiner

*Primary Examiner* — Tarifur Chowdhury
*Assistant Examiner* — Abdullahi Nur
(74) *Attorney, Agent, or Firm* — Harness, Dickey & Pierce, P.L.C.

(57) ABSTRACT

A spectroscopic image capturing apparatus including a light source section and an imaging section, wherein the light source section includes a light source portion, a first lens group, and a first polarizer, and the imaging section includes a second polarizer, a second lens group, an optical filter, and an imaging unit.

3 Claims, 5 Drawing Sheets

(VIEWED IN DIRECTION OF ARROW Wp)

(VIEWED IN DIRECTION OF ARROW Wr)

(VIEWED IN DIRECTION OF ARROW Wr)

SPECTROSCOPIC IMAGE CAPTURING APPARATUS

BACKGROUND

1. Technical Field

The present invention relates to a spectroscopic image capturing apparatus.

2. Related Art

As is known, it is sometimes desirable to acquire information on the components or content of an object while keeping the object intact. To accomplish this, there is a widely used method for capturing spectral image data on the object and analyzing the data to produce, for example, component information. For example, JP-A-2000-329617 discloses a method for acquiring spectral data on a specific portion of an object. In this method, an image data acquisition apparatus captures an image of the entire object to acquire an image of the object. Also, a spectral data acquisition apparatus acquires spectral data in an area narrower than the acquired image of the object and at a higher wavelength resolution than the image data acquisition apparatus. The image data acquisition apparatus is thus used to acquire general characteristics of the object, while the spectral data acquisition apparatus is used to analyze a characteristic portion of the data in detail and thereby acquire the analysis result. The spectroscopic image input system disclosed in JP-A-2000-329617 accommodates a unit that determines the specific portion and characterizes, that is, analyzes the object in a quick, stable manner without a human operator's judgment.

Further, JP-A-2009-33222 discloses an image capturing apparatus capable of producing a spectroscopic image of an object by using a single-panel digital camera but also using a spectroscopic filter having a narrow-band wavelength transmitting characteristic to acquire captured images of the object while changing the wavelength transmitting band and combining the acquired images of the wavelength bands.

In recent years, however, trends of maintaining health, ensuring food safety, and other requirements increasingly demand a compact food checker and other devices for measuring components, sugar content, and other parameters of a food product. The spectroscopic image input system disclosed in JP-A-2000-329617, however, not only requires the image capturing apparatus for acquiring an image of an entire object but also the spectral data acquisition apparatus for acquiring a spectral image of a specific portion of the object. This results in an increase in the size of the system. Further, providing a compact food checker allows the apparatus to capture an image of a close object, but measurement of food components and other parameters requires measurement of the interior of the object instead of the surface thereof. When a food product whose image is to be captured has a shiny surface, it is necessary to suppress an effect of light specularly reflected off the shiny surface. JP-A-2009-33222 suggests a method used with the image capturing apparatus for capturing an image of an object close thereto but does not disclose compensation for the effect of specular reflection.

SUMMARY

An advantage of some aspects of the invention is to provide a spectroscopic image capturing apparatus capable of suppressing the effect of specular reflection and accurately performing spectroscopic analysis of an object.

The invention can be implemented as the following forms or application examples.

Application Example 1

A spectroscopic image capturing apparatus according to this application example includes a light source section and an imaging section. The light source section includes a light source portion, a first lens group, and a first polarizer, and the imaging section includes a second polarizer, a second lens group, an optical filter, and an imaging unit.

According to the spectroscopic image capturing apparatus of this application example, when polarized light outputted from the first polarizer provided in the light source section is projected onto an object to be analyzed in terms of components, the polarized light reaches the interior of the object, and light reflected off internal components is outputted as depolarized light. On the other hand, light specularly reflected off the surface of the object is outputted as polarized light with its polarization maintained. The reflected light depolarized by the internal components of the object and the polarized light specularly reflected off the surface of the object are mixed to form analyzed light and are incident on the imaging section. The second polarizer provided in the imaging section absorbs the polarized light in the incident analyzed light, and only the reflected light depolarized by the internal components of the object reaches the imaging unit. As a result, the imaging unit can receive analyzed light free of the component specularly reflected off the surface of the object, whereby the spectroscopic image capturing apparatus can form an image of the object for accurate spectroscopic analysis.

Application Example 2

In the application example described above, each of the first polarizer and the second polarizer includes a linearly polarizing portion, and the first polarizer and the second polarizer are disposed so that the polarization direction of linearly polarized light produced by the first polarizer and the polarization direction of linearly polarized light produced by the second polarizer are perpendicular to each other.

The term "perpendicular" used in the application example described above does not mean exact 90-degree intersection but accepts a predetermined angular range around a target value of 90 degrees at least in consideration of positional precision in typical apparatus assembly or variations of parts themselves. According to the application example described above, since each of the first polarizer and the second polarizer is a linearly polarizing portion that polarizes light incident thereon into linearly polarized light, the amount of change (shift) in the polarization of the light specularly reflected off the surface of the object is small, whereby the imaging section can more reliably remove the specularly reflected light and the spectroscopic image capturing apparatus can hence form an image of the object for accurate spectroscopic analysis.

Application Example 3

In the application example described above, each of the linearly polarizing portions is a linearly polarizing plate.

According to the application example described above, the spectroscopic image capturing apparatus can be simply configured, and the polarization axes of the first polarizer and the second polarizer can be readily adjusted with respect to each other.

Application Example 4

In the application example described above, each of the first polarizer and the second polarizer include a circularly polarizing portion, and the first polarizer and the second polarizer are disposed so that the rotation direction of circularly polarized light produced by the first polarizer and the rotation direction of circularly polarized light produced by the second polarizer are the same direction.

According to the application example described above, since each of the first polarizer and the second polarizer is a circularly polarizing portion that polarizes light incident thereon into circularly polarized light, the amount of change (shift) in the polarization of the light specularly reflected off the surface of the object is small, whereby using circularly polarized light allows the imaging section to more reliably remove the specularly reflected light even when the positioning of the second polarizer around the optical axis is shifted and the spectroscopic image capturing apparatus can hence form an image of the object for accurate spectroscopic analysis.

Application Example 5

In the application example described above, each of the circularly polarizing portions includes a $\lambda/4$ retardation film.

According to the application example described above, since combining a $\lambda/4$ retardation film with a polarizing plate readily allows polarized light to be produced and the circularly polarizing portions of the first polarizer and the second polarizer can include the same circularly polarizing portion, the directions of circularly polarized light can be readily oriented in the same direction in the spectroscopic image capturing apparatus.

Application Example 6

In the application example described above, the optical filter is a variable wavelength optical filter.

According to the application example described above, using a variable wavelength optical filter, which allows selection of a wavelength region within which a spectroscopic image of a desired component from a variety of components contained in the object is acquired, allows a single spectroscopic image capturing apparatus to acquire a desired spectroscopic image.

Application Example 7

A spectroscopic image capturing apparatus according to this application example includes a light source, a first polarizer, a second polarizer, an optical filter, and an imaging unit. The first polarizer is disposed in a first optical path between the light source and an object to be imaged, and the second polarizer is disposed in a second optical path between the object to be imaged and the imaging unit.

According to the spectroscopic image capturing apparatus of this application example, when polarized light outputted from the first polarizer provided in the light source section is projected onto an object to be analyzed in terms of components, the polarized light reaches the interior of the object, and light reflected off internal components is outputted as depolarized light. On the other hand, light specularly reflected off the surface of the object is outputted as polarized light with its polarization maintained. The reflected light depolarized by the internal components of the object and the polarized light specularly reflected off the surface of the object are mixed to form analyzed light and are incident on the imaging unit. The second polarizer provided in the imaging section absorbs the polarized light in the incident analyzed light, and only the reflected light depolarized by the internal components of the object reaches the imaging unit. As a result, the imaging unit can receive analyzed light free of the component specularly reflected off the surface of the object, whereby the spectroscopic image capturing apparatus can form an image of the object for accurate spectroscopic analysis.

Application Example 8

In the application example described above, each of the first polarizer and the second polarizer include a linearly polarizing portion, and the first polarizer and the second polarizer are disposed so that the polarization direction of linearly polarized light produced by the first polarizer and the polarization direction of linearly polarized light produced by the second polarizer are perpendicular to each other.

The term "perpendicular" used in the application example described above also does not mean exact 90-degree intersection but accepts a predetermined angular range around a target value of 90 degrees at least in consideration of positional precision in typical apparatus assembly or variations of parts themselves. According to the application example described above, since each of the first polarizer and the second polarizer is a linearly polarizing portion that polarizes light incident thereon into linearly polarized light, the amount of change (shift) in the polarization of the light specularly reflected off the surface of the object is small, whereby the imaging unit can more reliably remove the specularly reflected light and the spectroscopic image capturing apparatus can hence form an image of the object for accurate spectroscopic analysis.

BRIEF DESCRIPTION OF THE DRAWINGS

The invention will be described with reference to the accompanying drawings, wherein like numbers reference like elements.

FIG. 1A is a block diagram of a schematic configuration of the apparatus; FIG. 1B is a block diagram of a light source section in the apparatus; and FIG. 1C is a block diagram of an imaging section in the apparatus.

FIG. 2A is a conceptual diagram schematically showing the relationship between light outputted from the light source section and light incident on the imaging section; and FIG. 2B schematically shows a light intensity distribution for describing specular reflection.

FIG. 4A is a block diagram of a schematic configuration of the apparatus; FIG. 4B is a block diagram of a light source section in the apparatus; and FIG. 4C is a block diagram of an imaging section in the apparatus.

FIG. 5A is a conceptual diagram schematically showing the relationship between light outputted from a light source section and light incident on an imaging section; and FIGS. 5B to 5D describe the direction of circularly polarized light.

DESCRIPTION OF EXEMPLARY EMBODIMENTS

Embodiments according to the invention will be described below with reference to the drawings.

First Embodiment

Figure 1A:
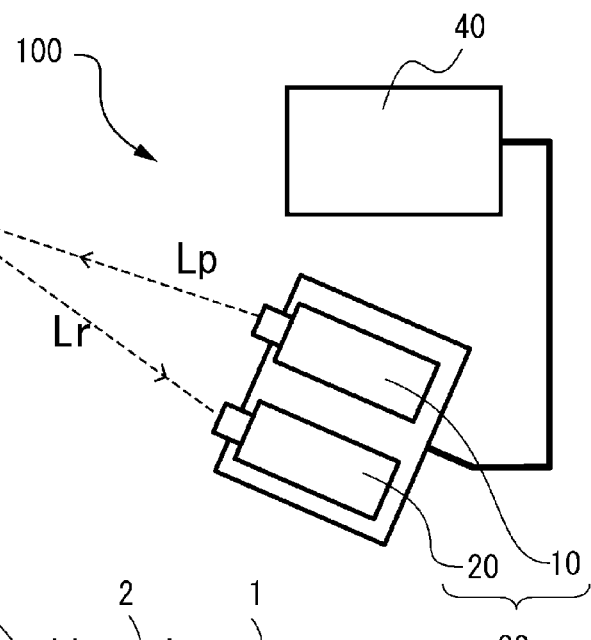
FIGS. 1A to 1C show a spectroscopic image capturing apparatus according to a first embodiment.
Figure 1B:
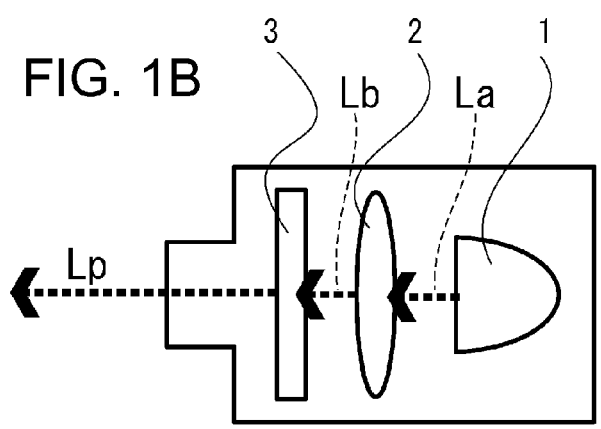
Figure 1C:
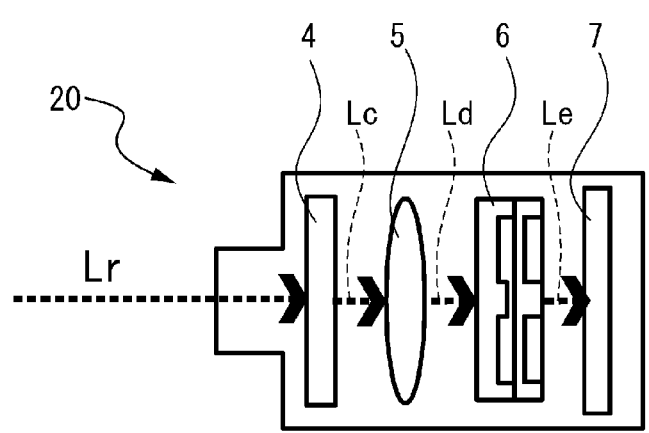

FIGS. 1A to 1C are block diagrams showing a schematic configuration of a spectroscopic image capturing apparatus according to a first embodiment. A spectroscopic image capturing apparatus 100 according to the first embodiment includes an image acquisition unit 30 (hereinafter referred to as a spectroscopic camera unit 30), which includes a light source section 10 and an imaging section 20, and a processing control unit 40, which controls the light source section 10 and performs image processing on an image produced by the imaging section 20, as shown in FIG. 1A.

The light source section 10 includes a light source portion 1, which includes a lamp that acts as a light source, a first lens group 2, which converts lamp light La from the light source portion 1 into parallelized light Lb, and a first polarizing plate 3, which forms a first polarizer and polarizes the parallelized light Lb from the first lens group 2 into linearly polarized light Lp, as shown in FIG. 1B. The lamp light La emitted from the light source portion 1 passes through the first lens group 2 and the first polarizing plate 3 and exits in the form of the linearly polarized light Lp toward an object M. The first lens group 2, which is drawn in the form of a single lens in FIG. 1B, is formed of a combination of a plurality of lenses.

The linearly polarized light Lp outputted from the light source section 10, the wavelength of which is selected as appropriate in accordance with what parameter of the object M is analyzed, is preferably infrared light, for example, when the object M is a food product and internal components thereof are analyzed. Visible light can alternatively be used when the color of the surface of the object M is measured. When infrared light is used, the light source portion 1 is a tungsten lamp, an infrared LED, or any other suitable light source.

The imaging section 20 includes a second polarizing plate 4, which forms a second polarizer and polarizes reflected light Lr from the object M into linearly polarized light Lc, a second lens group 5, which collects the linearly polarized light Lc into parallelized light Ld, an optical filter 6, which filters the parallelized light Ld from the second lens group 5 into analyzed light Le having a desired wavelength, and an imaging device 7, which serves as an imaging unit and captures an image formed of the analyzed light Le having a desired wavelength and having passed through the optical filter 6, as shown in FIG. 1C. The second lens group 5, which is drawn in the form of a single lens in FIG. 1C, is formed of a combination of a plurality of lenses.

Figure 2A:
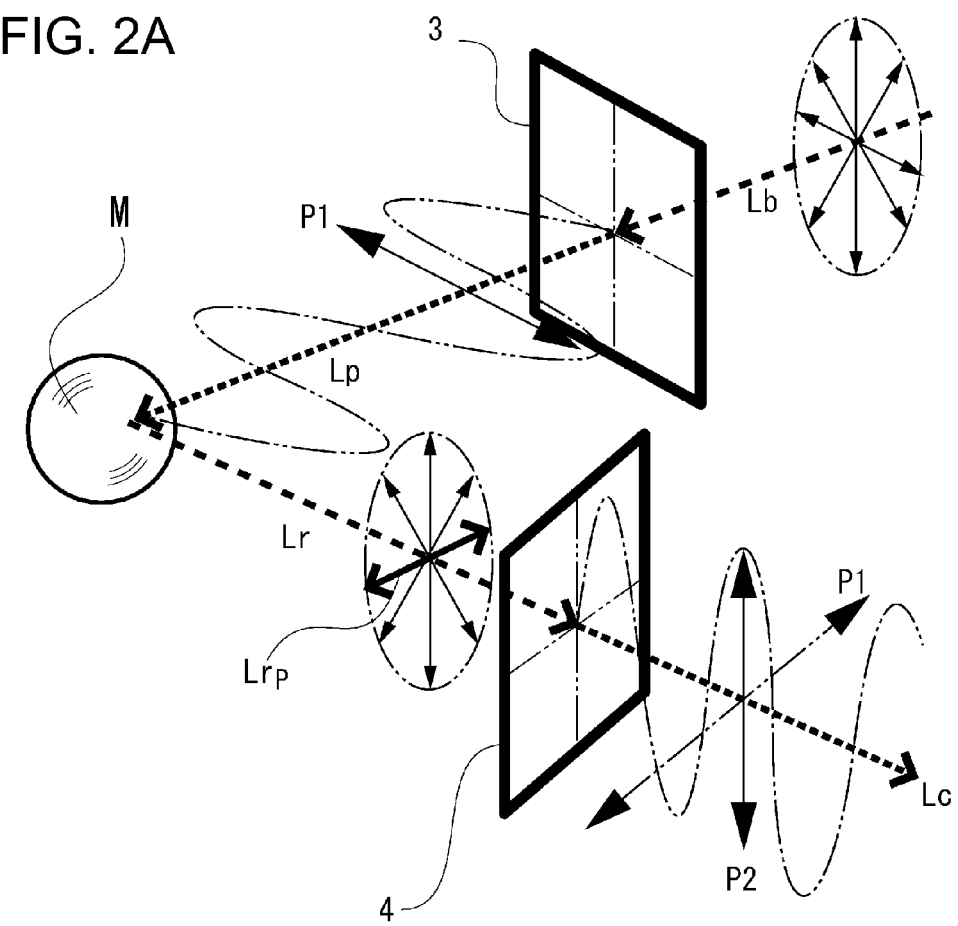
FIGS. 2A and 2B describe the spectroscopic image capturing apparatus according to the first embodiment.

FIG. 2A is a conceptual diagram schematically showing the relationship between the light outputted from the light source section 10 and the light incident on the imaging section 20. The parallelized light Lb formed from the light from the light source portion 1 that has passed through the first lens group 2 is a combination of light fluxes oscillating in all directions although they form parallelized light as a whole, as shown in FIG. 2A. The parallelized light Lb, after it passes through the first polarizing plate 3, which produces light polarized in a linear oscillation direction P1, forms the linearly polarized light Lp polarized in the linear oscillation direction P1, which is projected toward the object M.

Figure 2B:
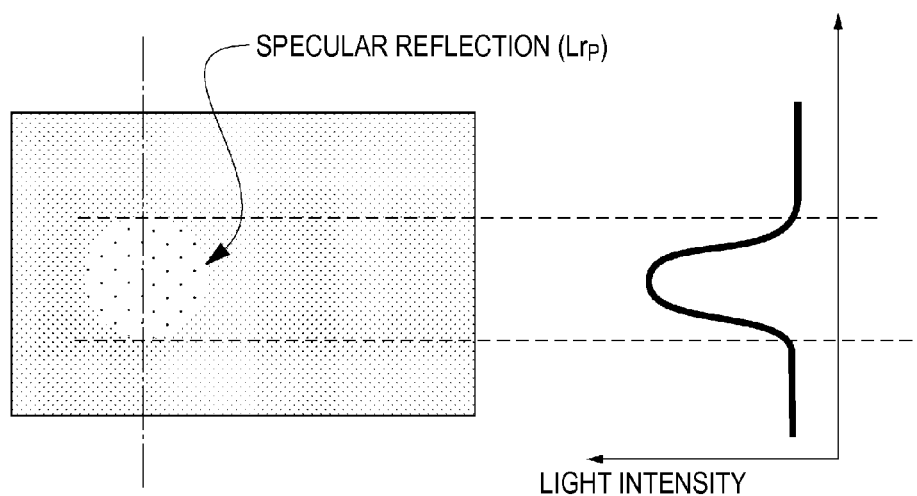

Since the linearly polarized light Lp projected onto the object M is light in the wavelength region of infrared light described above, the linearly polarized light Lp that impinges on the surface of the object M further reaches the interior thereof. The linearly polarized light Lp having reached the interior of the object M is repeatedly reflected in the interior of the object M and therefore depolarized, and the depolarized light is reflected in the form of reflected light Lr, which is a combination of light fluxes oscillating in all directions. The reflected light Lr, however, contains polarized reflected light $Lr_P$, which is the linearly polarized light Lp specularly reflected off the surface of the object M. The polarized reflected light $Lr_P$, which has been specularly reflected, has a higher intensity in the intensity distribution of the light projected onto the imaging device 7 shown in FIG. 1C, that is, the light intensity distribution of the reflected light Lr, than the light intensities in the other region containing no specular reflection, as shown in FIG. 2B. The presence of a portion having a high light intensity due to the specular reflection produces a large error in a spectroscopic image showing internal components of the object M.

To address the problem, the second polarizing plate provided in the imaging section 20, which receives the reflected light Lr, is disposed so that the polarization axis of the second polarizing plate 4 is oriented in a polarization direction P2, which is perpendicular to the polarization axis of the first polarizer plate 3, that is, the polarization direction P1, as shown in FIG. 2A. As a result, the linearly polarized light Lc free of the polarized reflected light $Lr_P$, which is the specular reflection component, is produced. A spectroscopic image produced by the linearly polarized light Lc having passed through the second lens group 5 and the optical filter 6, which is the analyzed light Le, can thus be an image having a small amount of significant deviation in the light intensity distribution. A spectroscopic image from which a more accurate analysis result is derived can therefore be produced.

Figure 3:
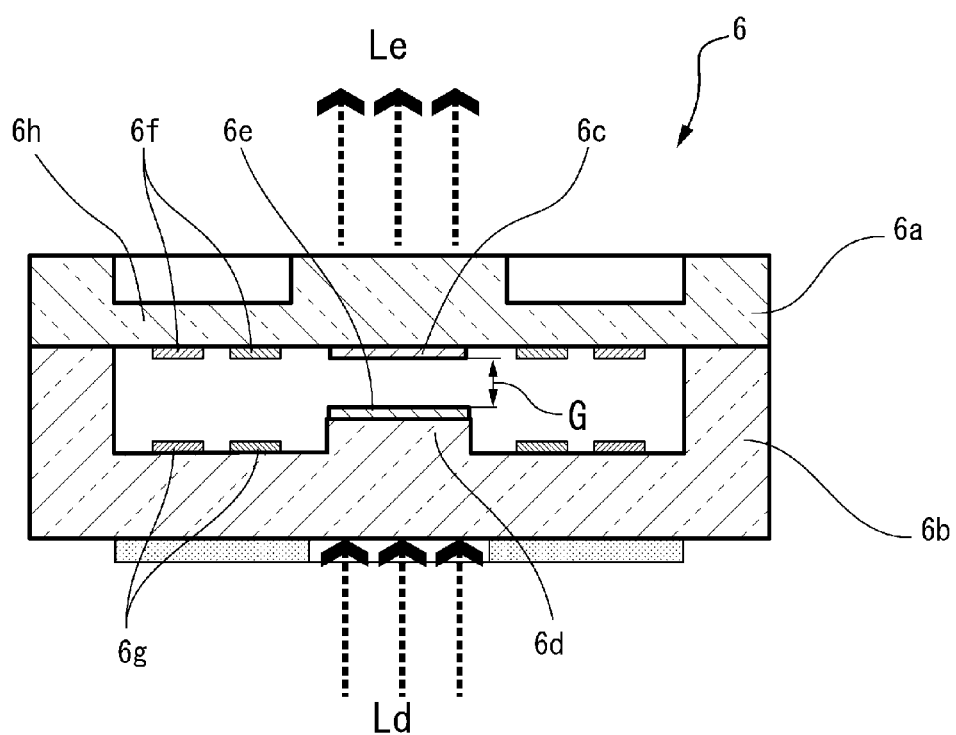
FIG. 3 is a cross-sectional view of a schematic configuration of an optical filter provided in the spectroscopic image capturing apparatus according to the first embodiment.

The incident light having passed through the second polarizing plate 4 and forming the linearly polarized light Lc is collected by the second lens group 5 to form the parallelized light Ld, which is guided to the optical filter 6, as shown in FIG. 1C. In this embodiment, the optical filter 6 is described based on a variable wavelength optical filter. A variable wavelength optical filter is also known as an etalon filter, and FIG. 3 is a schematic cross-sectional view of an etalon filter. The optical filter 6, which is a variable wavelength optical filter, is formed by bonding a first substrate 6a and a second substrate 6b to each other, as shown in FIG. 3. Each of the first substrate 6a and the second substrate 6b is formed of a transparent member made of, for example, soda glass, crystalline glass, quartz glass, lead glass, potassium glass, borosilicate glass, no-alkali glass, and a variety of other types of glass or quartz and other light-transmissive materials.

A first reflection film 6c is formed on a surface of the first substrate 6a in a central portion thereof that faces the second substrate 6b, and a second reflection film 6e is formed on the upper surface of an internal protrusion 6d of the second substrate 6b that faces the first reflection film 6c. Each of the reflection films 6c and 6e is formed of a dielectric multilayer film produced by alternately stacking a high-refractive-index layer and a low-refractive-index layer multiple times. To use the optical filter 6 in a visible or infrared wavelength region, the high-refractive-index layer of the dielectric multilayer film is made of, for example, titanium dioxide ($TiO_2$), tantalum pentoxide ($Ta_2O_5$), and niobium pentoxide ($Nb_2O_5$), and the low-refractive-index layer of the dielectric multilayer film is made of, for example, magnesium fluoride ($MgF_2$) and silicon dioxide ($SiO_2$). To use the optical filter 6 in an ultraviolet wavelength region, the high-refractive-index layer is made of, for example, aluminum oxide ($Al_2O_3$), hafnium oxide ($HfO_2$), zirconium dioxide ($ZrO_2$), and thorium oxide ($ThO_2$), and the low-refractive-index layer is made of, for example, magnesium fluoride ($MgF_2$) and silicon dioxide ($SiO_2$). Each of the reflection films 6c and 6e may alternatively be formed of a metal-based reflection film made of, for example, silver.

Annular first electrodes 6f are formed around the outer circumference of the first reflection film 6c on the first substrate 6a. Second electrodes 6g, which face the first electrodes 6f, are formed on the second substrate 6b. A current flows through the first electrodes 6f and the second electrodes 6g under the control of the processing control unit 40 shown in FIG. 1A so that a force that attracts the first electrodes 6f and the second electrodes 6g to each other is produced in accordance with the magnitude of the current, the direction thereof, and other factors. The area of the first substrate 6a where the first electrodes 6f are formed forms an annular thin portion 6h, which is bent by the attractive force. The distance G (hereinafter referred to as a gap G) between the first reflection film 6c and the second reflection film 6e are arbitrarily changed so that multiple beam interference occurs in the gap G and the incident parallelized light Ld is filtered so that the analyzed light Le having a predetermined wavelength is outputted.

The analyzed light Le is converted into an image signal by the imaging device 7 formed of, for example, a CCD (charge coupled device) image sensor, as shown in FIG. 1C. Specifically, the optical filter 6 is driven to separate the analyzed light Le into N light fluxes having wavelengths that are different from each other, that is, analyzed light fluxes $Le_1, Le_2, \ldots, Le_N$, and image signals based on the analyzed light fluxes $Le_1, Le_2, \ldots, Le_N$ are sent to the processing control unit 40. Predetermined analyzed images (data) are thus created. The N analyzed light fluxes $Le_1, Le_2, \ldots, Le_N$ are produced from the reflected light Lr by extracting light fluxes having wavelengths characterized by primary components of the object M and undergo image processing in the processing control unit 40. The resultant spectroscopic images are outputted as data.

As described above, the spectroscopic image capturing apparatus 100 according to the first embodiment can produce the analyzed light Le free of the specular reflection component from the object M based on the configuration in which the polarization direction of the first polarizing plate 3 provided in the light source section 10 and the polarization direction of the second polarizing plate 4 provided in the imaging section 20 are perpendicular to each other. An image for precise spectroscopic analysis can therefore be produced. Since the configuration further allows specular reflection to be readily removed, the apparatus can be configured so that the angle θ between the optical axis of the linearly polarized light Lp, which is outgoing light, and the optical axis of the reflected light Lr shown in FIG. 2A is set at an acute angle close to zero degrees, which causes the apparatus to receive a large amount of specular reflection. The size of the spectroscopic camera unit 30 can therefore be further reduced, as shown in FIG. 1A. For example, the spectroscopic camera unit 30 can be held by hand, as a typical digital camera, for analysis imaging. Further, integrating the processing control unit 40 with the spectroscopic camera unit 30 can even make the spectroscopic image capturing apparatus 100 portable.

Second Embodiment

As a second embodiment, a description will be made of a spectroscopic image capturing apparatus 200 that is different from the spectroscopic image capturing apparatus 100 according to the first embodiment in terms of the first polarizer plate 3 and the second polarizer plate 4 provided therein. In the spectroscopic image capturing apparatus 200 according to the second embodiment, the same components as those of the spectroscopic image capturing apparatus 100 according to the first embodiment have the same reference characters and no description of the same components will be made in some cases.

Figure 4A:
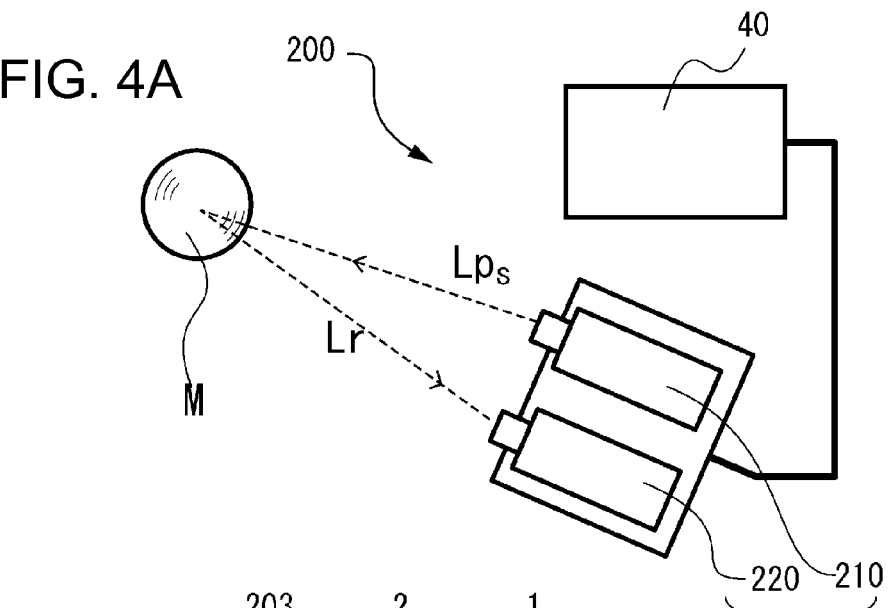
FIGS. 4A to 4C show a spectroscopic image capturing apparatus according to a second embodiment.
Figure 4B:
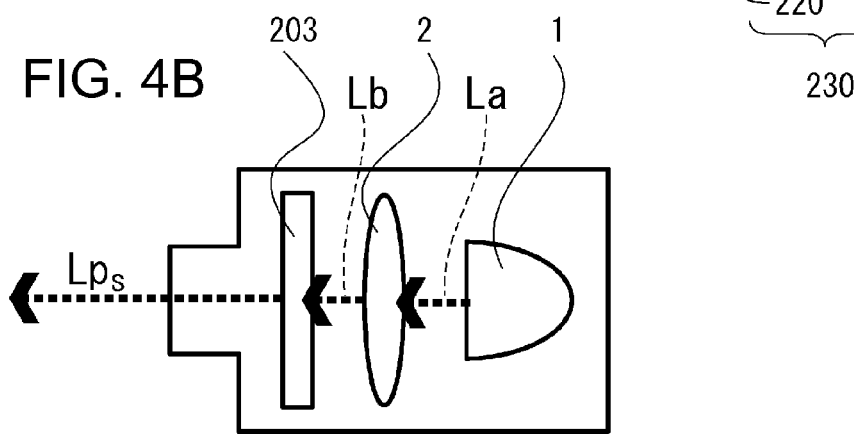
Figure 4C:
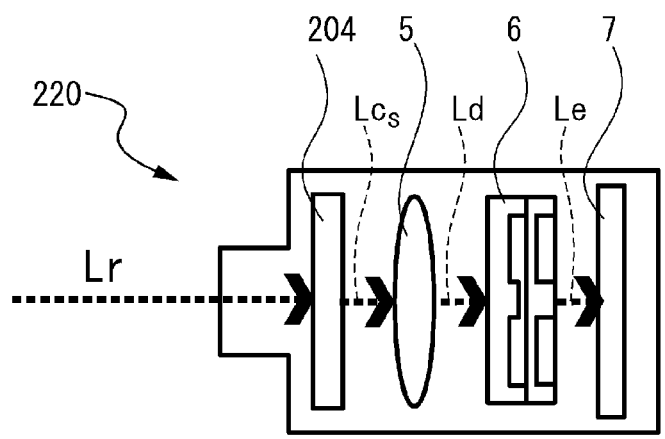

FIGS. 4A to 4C show the spectroscopic image capturing apparatus 200 according to the second embodiment. FIG. 4A is a block diagram showing a schematic configuration of the apparatus. FIG. 4B is a block diagram showing the configuration of a light source section in the apparatus. FIG. 4C is a block diagram showing the configuration of an imaging section in the apparatus. The spectroscopic image capturing apparatus 200 has the same configuration as that of the spectroscopic image capturing apparatus 100 described in the first embodiment as shown in FIG. 4A, but a light source section 210 and an imaging section 220 provided in a spectroscopic camera unit 230 include a first circularly polarizing plate 203 and a second circularly polarizing plate 204 for producing circular polarization respectively, as shown in FIGS. 4B and 4C. The light source section 210, in which the light emitted from the light source portion 1 is circularly polarized by the first circularly polarizing plate 203, outputs circularly polarized light $Lp_S$. The outputted circularly polarized light $Lp_S$ is reflected off an object M and forms reflected light Lr, which is separated into right-handed circularly polarized light and left-handed circularly polarized light by the second circularly polarizing plate 204. The second circularly polarizing plate 204 transmits only one of the two types of circularly polarized light, circularly polarized light $Lc_S$, which is collected by the second lens group 5, and the resultant parallelized light Ld is guided to the optical filter 6. The optical filter 6 produces analyzed light Le having a desired wavelength, from which the imaging device 7 produces image data. Each of the circularly polarizing plates 203 and 204 can be a polarizing plate formed of a linearly polarizing plate to which a λ/4 retardation film is bonded with its axis inclined to the linearly polarizing plate by 45 degrees. The thus formed polarizing plate can produce and output circularly polarized light.

Figure 5A:
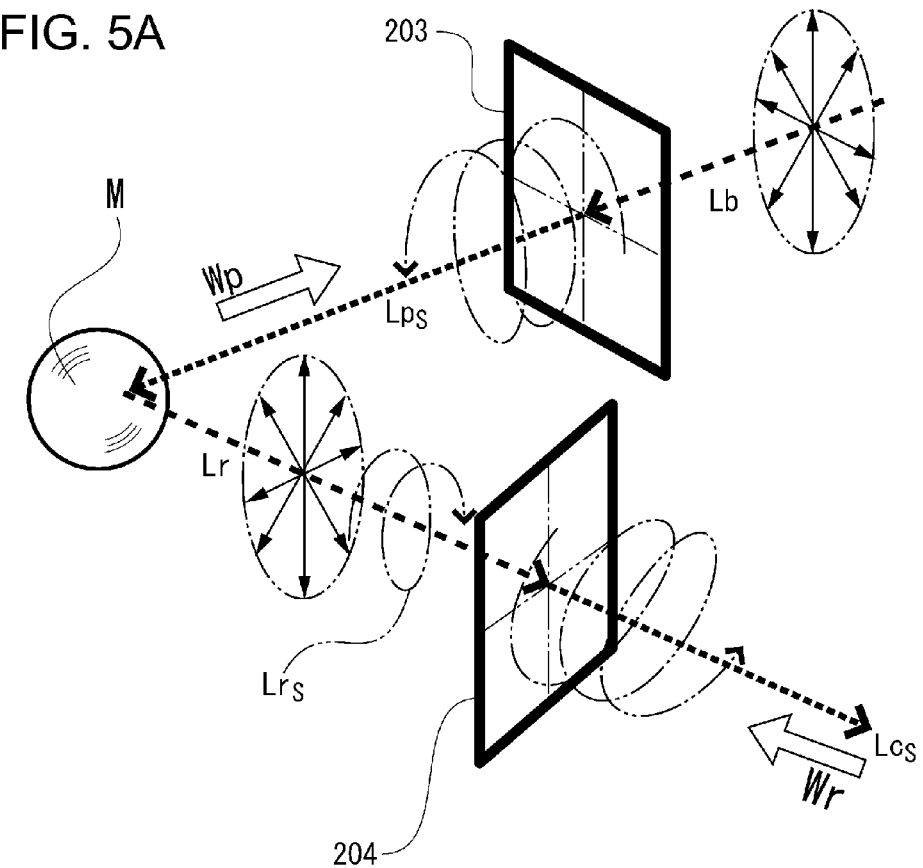
FIGS. 5A to 5D describe the spectroscopic image capturing apparatus according to the second embodiment.
Figure 5B:
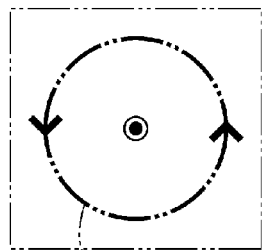

FIGS. 5A to 5D are conceptual diagrams schematically showing the relationship between the light outputted from the light source section 210 and the light incident on the imaging section 220. As shown in FIG. 5A, the parallelized light Lb having passed through the first lens group 2 passes through the first circularly polarizing plate 203 including the λ/4 retardation film so that the parallelized light Lb is converted into the circularly polarized light $Lp_S$, which is outputted and applied to the object M. In this embodiment, the circularly polarized light $Lp_S$ is polarized so that it rotates in the left-handed rotation direction as shown in FIG. 5B viewed in the direction of the arrow Wp along the optical axis of the circularly polarized light $Lp_S$ shown in FIG. 5A.

Figure 5C:
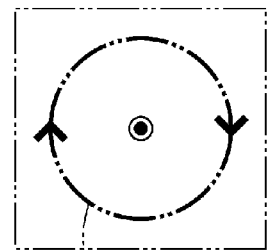

The circularly polarized light $Lp_S$, when applied to the object M, reaches the interior of the object M and is reflected off the object M to form the reflected light Lr. Since the circularly polarized light $Lp_S$ is depolarized in the interior of the object M, the reflected light Lr is a combination of light fluxes oscillating in all directions. The reflected light Lr, however, contains circularly polarized reflected light $Lr_S$, which is the circularly polarized light $Lp_S$ specularly reflected off the surface of the object M. In this embodiment, the circularly polarized reflected light $Lr_S$ is reflected so that it rotates in the right-handed rotation direction as shown in FIG. 5C viewed in the direction of the arrow Wr along the optical axis of the reflected light Lr shown in FIG. 5A. That is, the specularly reflected light $Lr_S$ forms the circularly polarized light $Lr_S$ rotating in the direction opposite to the rotation direction of the outputted circularly polarized light $Lp_S$.

Figure 5D:
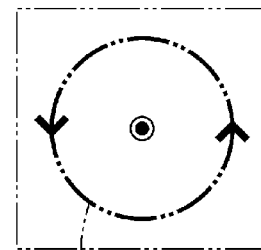

The reflected light Lr is incident on the second circularly polarizing plate 204. The second circularly polarizing plate 204 polarizes the reflected light Lr into circularly polarized light $Lc_S$ rotating in the left-handed rotation direction as shown in FIG. 5D viewed in the direction of the arrow Wr along the optical axis of the reflected light Lr shown in FIG. 5A. The circularly polarized reflected light $Lr_S$ contained in the reflected light Lr incident on the second circularly polarizing plate 204 is therefore absorbed by the second circularly polarizing plate 204, which polarizes light incident thereon into polarized light rotating in the direction opposite to the rotation direction of the circularly polarized reflected light $Lr_S$.

As described above, in the spectroscopic image capturing apparatus 200 according to the second embodiment, the analyzed light Le free of the specularly reflected component from the object M can be produced by setting the rotation direction of the circularly polarized light outputted from the first circularly polarizing plate 203 provided in the light source section 210 to be the same as the rotation direction of the circularly polarized light outputted from the second circularly polarizing plate 204 provided in the imaging section 220. An image for precise spectroscopic analysis can therefore be produced. The spectroscopic image capturing apparatus 200 according to the second embodiment has been described with reference to the case where the circularly polarized light $Lp_S$ rotates in the left-handed rotation direction in FIG. 5B, the circularly polarized reflected light $Lr_S$ rotates in the right-handed rotation direction in FIG. 5C, and the circularly polarized light $Lc_S$ rotates in the left-handed rotation direction in FIG. 5D. The rotation directions are not limited to those described above, and the circularly polarized light $Lp_S$ and the circularly polarized light $Lc_S$ only need to rotate in the same rotation direction.

The first polarizing plate 3 in the spectroscopic image capturing apparatus 100 according to the first embodiment described above may alternatively be a polarization conversion element, such as a PSB (polarized beam splitter). Using a polarization conversion element reduces the decrease in the amount of outputted light Lp from the light source section 10, whereby the brightness, contrast, and other image-quality-related parameters of an analyzed image can be increased. A spectroscopic image capturing apparatus capable of performing more accurate analysis can thus be provided.

The entire disclosure of Japanese Patent Application No. 2012-148202 filed Jul. 2, 2012 is expressly incorporated by reference herein.

What is claimed is:

1. A spectroscopic image capturing apparatus comprising:
a light source device that includes:
a light source,
a first lens group that receives light from the light source and that outputs a first parallel light, and
a first polarizer that receives the first parallel light from the first lens group and that outputs a first circular polarized light toward an object; and
an imaging device that optically communicates with the light source device, the imaging device includes:
a second polarizer that receives a circular polarized reflection light, which results from reflecting the first circular polarized light by the object, and that outputs a second circular polarized light,
a second lens group that receives the second circular polarized light from the second polarizer and that outputs a second parallel light,
an optical filter that receives the second parallel light from the second lens group and that outputs an analyzed light having a desired wavelength, and
an imaging unit that receives the analyzed light from the optical filter and that produces image data, wherein
the first circular polarized light has a first circular polarization direction,
the second circular polarized light has a second circular polarization direction, the second circular polarization direction is the same direction as the first circular polarization direction,
the circular polarized reflection light has a third circular polarization direction, the third circular polarization direction is a different direction than the first and second circular polarization directions, and
the optical filter is an etalon filter.

2. The spectroscopic image capturing apparatus according to claim 1, wherein
each of the first and second polarizers includes a λ/4 retardation film.

3. The spectroscopic image capturing apparatus according to claim 1, wherein
the etalon filter includes:
first and second substrates facing each other,
a first reflection film that is formed on the first substrate,
a second reflection film that is formed on the second substrate and that faces the first reflection film,
a first electrode that is formed on the first substrate and that is located outside of the first reflection film,
a second electrode that is formed on the second substrate and that is located outside of the second reflection film, and
a gap that is provided between the first and second reflection films,
each of the first and second reflection films includes a stack layer that is formed by alternatively stacking a high-reflective-index layer and a low-reflective-index layer, and
a dimension of the gap is varied by flowing an electric current in the first and second electrodes.

* * * * *